US009468735B2

(12) United States Patent
Grychowski et al.

(10) Patent No.: US 9,468,735 B2
(45) Date of Patent: Oct. 18, 2016

(54) VENTILATOR CIRCUIT AND METHOD FOR THE USE THEREOF

(71) Applicant: TRUDELL MEDICAL INTERNATIONAL, London (CA)

(72) Inventors: Jerry R. Grychowski, Lake Zurich, IL (US); Martin P. Foley, London (CA)

(73) Assignee: Trudell Medical International, London (CA)

( * ) Notice: Subject to any disclaimer, the term of this patent is extended or adjusted under 35 U.S.C. 154(b) by 0 days.

(21) Appl. No.: 14/539,600

(22) Filed: Nov. 12, 2014

(65) Prior Publication Data

US 2015/0196729 A1 Jul. 16, 2015

Related U.S. Application Data

(63) Continuation of application No. 13/231,298, filed on Sep. 13, 2011, now Pat. No. 8,905,026, which is a continuation of application No. 11/410,270, filed on Apr. 24, 2006, now Pat. No. 8,028,697.

(60) Provisional application No. 60/675,944, filed on Apr. 28, 2005.

(51) Int. Cl.
*A61M 16/14* (2006.01)
*A61M 15/00* (2006.01)
(Continued)

(52) U.S. Cl.
CPC ......... *A61M 16/14* (2013.01); *A61M 15/0015* (2014.02); *A61M 15/0018* (2014.02); *A61M 15/0021* (2014.02); *A61M 15/0086* (2013.01); *A61M 16/04* (2013.01); *A61M 16/06* (2013.01); *A61M 16/0816* (2013.01);

(Continued)

(58) Field of Classification Search
CPC .... A61M 11/00; A61M 11/08; A61M 15/00; A61M 16/00; A61M 16/08; A61M 16/0816; A61M 16/0875; A61M 16/10; A61M 16/14; A61M 16/20; A61M 16/208
See application file for complete search history.

(56) References Cited

U.S. PATENT DOCUMENTS

| 2,417,759 A | 3/1947 | Johnson |
| 3,028,873 A | 4/1962 | Kindred |

(Continued)

FOREIGN PATENT DOCUMENTS

| CA | 2 210 721 A1 | 7/1996 |
| CA | 2 329 126 A1 | 10/1999 |

(Continued)

OTHER PUBLICATIONS

"A Dose-ranging study to assess the effect of inhaled corticosteroids in ventilated preterm neonates.," Drs. Vibhuti Shah and Edmond Kelly, Mount Sinai Hospital, and Dr. Michael Dunn, Sunnybrook and Women's College Health Sciences Center, date unknown, 27 pages.

(Continued)

*Primary Examiner* — Rachel Young
(74) *Attorney, Agent, or Firm* — Brinks Gilson & Lione

(57) ABSTRACT

A ventilator circuit for use in administering medication to a patient includes a housing, a one-way inhalation valve and a one-way exhalation valve. A metered does inhaler receptacle is in fluid flow communication with an interior space of the housing holding chamber. An exhaust conduit communicates between input and output passageways disposed on opposite sides of the interior space.

17 Claims, 8 Drawing Sheets

(51) Int. Cl.
*A61M 16/08* (2006.01)
*A61M 16/20* (2006.01)
*A61M 16/04* (2006.01)
*A61M 16/06* (2006.01)

(52) U.S. Cl.
CPC ....... *A61M 16/208* (2013.01); *A61M 15/0065* (2013.01); *A61M 16/08* (2013.01); *A61M 2205/0233* (2013.01); *A61M 2240/00* (2013.01)

(56) References Cited

U.S. PATENT DOCUMENTS

| | | |
|---|---|---|
| 3,183,906 A | 5/1965 | Moyat |
| 3,667,475 A | 6/1972 | Venturelli et al. |
| 3,726,274 A | 4/1973 | Bird et al. |
| 3,842,828 A | 10/1974 | Bird |
| 4,240,417 A | 12/1980 | Holever |
| 4,417,574 A | 11/1983 | Talonn et al. |
| 4,457,305 A | 7/1984 | Shanks et al. |
| 4,534,343 A | 8/1985 | Nowacki et al. |
| 4,803,977 A | 2/1989 | Kremer et al. |
| 4,815,459 A | 3/1989 | Beran |
| 4,828,844 A | 5/1989 | Rontgen-Odenthal et al. |
| 4,938,210 A * | 7/1990 | Shene ............... A61M 15/0086 128/200.23 |
| 5,002,048 A | 3/1991 | Makiej, Jr. |
| 5,005,572 A | 4/1991 | Raemer et al. |
| 5,006,343 A | 4/1991 | Benson et al. |
| 5,012,804 A | 5/1991 | Foley et al. |
| 5,044,361 A | 9/1991 | Werner et al. |
| 5,049,388 A | 9/1991 | Knight et al. |
| 5,131,387 A | 7/1992 | French et al. |
| 5,164,369 A | 11/1992 | Cochrane et al. |
| 5,178,138 A | 1/1993 | Walstrom et al. |
| 5,228,436 A | 7/1993 | Parkin |
| 5,230,884 A | 7/1993 | Evans et al. |
| 5,260,273 A | 11/1993 | Cochrane et al. |
| 5,262,405 A | 11/1993 | Girod-Vaquez et al. |
| 5,292,499 A | 3/1994 | Evans et al. |
| 5,299,566 A | 4/1994 | Davis et al. |
| 5,309,903 A | 5/1994 | Long |
| 5,320,096 A | 6/1994 | Hans |
| 5,355,872 A | 10/1994 | Riggs et al. |
| 5,357,946 A | 10/1994 | Kee et al. |
| 5,407,914 A | 4/1995 | Cochrane et al. |
| 5,433,195 A | 7/1995 | Kee et al. |
| 5,471,979 A | 12/1995 | Psaros et al. |
| 5,474,759 A | 12/1995 | Fass |
| 5,479,920 A | 1/1996 | Piper et al. |
| 5,546,930 A | 8/1996 | Wikefeldt |
| 5,590,644 A | 1/1997 | Rosenkoetter |
| 5,616,158 A | 4/1997 | Biendarra et al. |
| 5,657,750 A | 8/1997 | Colman et al. |
| 5,666,946 A | 9/1997 | Langenback |
| 5,693,944 A | 12/1997 | Rich |
| 5,720,282 A | 2/1998 | Wright |
| 5,743,251 A | 4/1998 | Howell et al. |
| 5,789,381 A | 8/1998 | Cochrane et al. |
| 5,816,240 A | 10/1998 | Komesaroff |
| 5,829,428 A | 11/1998 | Waters et al. |
| 5,848,587 A | 12/1998 | King |
| 5,853,003 A | 12/1998 | Faithful et al. |
| 5,925,334 A | 7/1999 | Rubin et al. |
| 6,014,972 A | 1/2000 | Sladek |
| 6,039,042 A | 3/2000 | Sladek |
| 6,269,810 B1 | 8/2001 | Brooker et al. |
| 6,279,574 B1 | 8/2001 | Richardson et al. |
| 6,309,623 B1 | 10/2001 | Weers et al. |
| 6,309,624 B1 | 10/2001 | Sapsford et al. |
| 6,315,983 B1 | 11/2001 | Eistetter |
| 6,390,091 B1 | 5/2002 | Banner et al. |
| 6,435,177 B1 | 8/2002 | Schmidt et al. |
| 6,451,339 B2 | 9/2002 | Patel et al. |
| 6,494,203 B1 | 12/2002 | Palmer |
| 6,503,481 B1 | 1/2003 | Thurston et al. |
| 6,524,557 B1 | 2/2003 | Bäckström et al. |
| 6,527,011 B1 | 3/2003 | Mantz |
| 6,550,476 B1 | 4/2003 | Ryder |
| 6,572,841 B1 | 6/2003 | Mautone |
| 6,575,944 B1 | 6/2003 | McNary et al. |
| 6,579,254 B1 | 6/2003 | McNary et al. |
| 6,581,600 B2 | 6/2003 | Bird |
| 6,613,734 B2 | 9/2003 | Cochrane et al. |
| 6,615,824 B2 | 9/2003 | Power |
| 6,622,725 B1 | 9/2003 | Fisher et al. |
| 6,635,283 B2 | 10/2003 | Edwards et al. |
| 6,645,467 B2 | 11/2003 | Mautone |
| 6,660,715 B2 | 12/2003 | Klibanov |
| 6,737,044 B1 | 5/2004 | Dickinson et al. |
| 6,770,619 B2 | 8/2004 | Larsson et al. |
| 6,805,118 B2 | 10/2004 | Brooker et al. |
| 6,886,561 B2 | 5/2005 | Bayron et al. |
| 6,921,527 B2 | 7/2005 | Platz et al. |
| 7,040,314 B2 | 5/2006 | Nguyen et al. |
| 7,201,164 B2 | 4/2007 | Grychowski et al. |
| 7,201,167 B2 | 4/2007 | Fink et al. |
| 7,219,668 B2 | 5/2007 | Flynn |
| 7,360,541 B2 | 4/2008 | Dhuper et al. |
| 2002/0069870 A1 | 6/2002 | Farmer |
| 2002/0104531 A1 | 8/2002 | Malone |
| 2002/0108614 A1 | 8/2002 | Schultz |
| 2003/0131844 A1 | 7/2003 | Kumar et al. |
| 2003/0136399 A1 | 7/2003 | Foley et al. |
| 2004/0003808 A1 | 1/2004 | Fuhrman et al. |
| 2004/0011364 A1 | 1/2004 | Dhuper et al. |
| 2005/0005929 A1 | 1/2005 | Snyder et al. |
| 2005/0011514 A1 | 1/2005 | Power et al. |
| 2005/0039746 A1 | 2/2005 | Grychowski et al. |
| 2005/0061314 A1 | 3/2005 | Davies et al. |
| 2005/0066964 A1 | 3/2005 | Bathe |
| 2005/0139211 A1 | 6/2005 | Alston et al. |
| 2005/0172954 A1 | 8/2005 | Smith et al. |
| 2005/0178383 A1 | 8/2005 | Mackie et al. |
| 2005/0199236 A1 | 9/2005 | Fink et al. |
| 2005/0205099 A1 | 9/2005 | Fink et al. |
| 2005/0217666 A1 | 10/2005 | Fink et al. |
| 2005/0217667 A1 | 10/2005 | Dhuper et al. |
| 2005/0229926 A1 | 10/2005 | Fink et al. |
| 2005/0229927 A1 | 10/2005 | Fink et al. |
| 2005/0229928 A1 | 10/2005 | Ivri et al. |
| 2005/0247312 A1 | 11/2005 | Davies |
| 2005/0274378 A1 | 12/2005 | Bonney et al. |
| 2006/0078506 A1 | 4/2006 | Niven et al. |
| 2006/0120968 A1 | 6/2006 | Niven et al. |
| 2008/0000470 A1 | 1/2008 | Minocchieri et al. |
| 2008/0017198 A1 | 1/2008 | Ivri |
| 2008/0264412 A1 | 10/2008 | Meyer et al. |
| 2009/0025722 A1 | 1/2009 | Peiper et al. |

FOREIGN PATENT DOCUMENTS

| | | |
|---|---|---|
| CA | 2 354 561 A1 | 6/2000 |
| CA | 2 493 078 A1 | 2/2004 |
| CA | 2 515 593 A1 | 8/2004 |
| CA | 2 424 731 A1 | 10/2004 |
| EP | 0 242 790 A2 | 10/1987 |
| EP | 0 281 650 A1 | 9/1988 |
| EP | 0 284 227 A2 | 9/1988 |
| EP | 0 460 731 A1 | 12/1991 |
| EP | 0 549 266 A2 | 6/1993 |
| EP | 0 972 534 A2 | 1/2000 |
| EP | 0 972 534 A3 | 1/2000 |
| EP | 1 222 940 A2 | 7/2002 |
| FR | 1 416 169 A | 10/1965 |
| GB | 750 152 A | 6/1953 |
| GB | 2 272 745 A | 5/1994 |
| WO | WO 00/45884 A1 | 8/2000 |
| WO | WO 01/78819 A1 | 10/2001 |
| WO | WO 03/013340 A2 | 2/2003 |
| WO | WO 03/047674 A1 | 6/2003 |
| WO | WO 2004/011071 A1 | 2/2004 |
| WO | WO 2004/071549 A2 | 8/2004 |
| WO | WO 2006/026237 A1 | 3/2006 |

(56) References Cited

FOREIGN PATENT DOCUMENTS

| WO | WO 2006/114699 A2 | 11/2006 |
|---|---|---|
| WO | WO 2007/030162 A2 | 3/2007 |
| WO | WO 2008/028092 A2 | 3/2008 |
| WO | WO 2008/042912 A2 | 4/2008 |

OTHER PUBLICATIONS

Amirav, I. et al., "Nebuliser hood compared to mask in wheezy infants: aerosol therapy without tears!," Arch. Dis. Child, vol. 88, 2003, pp. 719-723.
Ballard, Julie et al., "A survey of albuterol administration practices in intubated patients in the neonatal intensive care unit," Respiratory Care, Jan. 2002, 47(1), pp. 31-38.
Bambang, Sidarto Oetomo et al., "Surfactant Nebulization does not Alter Airflow Obstruction and Bronchial Responsiveness to Histamine in Asthmatic Children," Am. J. Respir. Crit. Care Med., vol. 153, 1996, pp. 1148-1152.
Beck, Jennifer et al., "Prolonged Neural Expiratory Time Induced by Mechanical Ventilation in Infants," Pediatric Research, vol. 55, No. 5, 2004, pp. 747-754.
Becquemin, M.H. et al., "Particle deposition and resistance in the nose of adults and children," Eur. Respir. J., vol. 4, 1991, pp. 694-702.
Berggren, Acta Paediatr, Pilot study of nebulized surfactant therapy for neonatal respiratory distress syndrome, 2000, vol. 89, pp. 460-464.
Cheifetz, Ira M. MD, "Invasive and Noninvasive Pediatric Mechanical Ventilation," Respiratory Care, vol. 48, No. 4, Apr. 2003, pp. 442-458.
Cole, Cynthia H., M.D., M.P.H., "The Use of Aerosolized Medicines in Neonates,", Neonatal Respiratory Diseases, vol. 10, No. 4; Associates in Medical Marketing Co., Inc., Newtown, PA.; 2000, 6 pages.
Dijk, P.H. et al., "Surfactant nebulisation: safety, efficiency and influence on surface lowering properties and biochemical composition," Intensive Care Med., vol. 23, 1997, pp. 456-462.
Dolovich, M., "Influence of inspiratory flow rate, particle size, and airway caliber on aerosolized drug delivery to the lung," Respiratory Care, 2000, vol. 45(6): pp. 597-608.
Dubus, Jean C. et al., "Aerosol Deposition in Neonatal Ventilation," Pediatric Research, vol. 58, No. 1, 2005, pp. 10-14.
Final Office Action for U.S. Appl. No. 10/774,751, dated Jun. 24, 2009, 8 pages.
Fink, J.B. et al. "Device and equipment evaluations," Respir. Care, 2004, 49(10), pp. 1157-1164.
Fink, J.B. et al., "Can high efficiency aerosol delivery continue after extubation?" Critical Care, 2005, 9(Suppl1): p. P129.
Fink, James B., "Aerosol Delivery to Ventilated Infant and Pediatric Patients," Respiratory Care, vol. 49, No. 6, Jun. 2004, pp. 653-665.
Foust, Gregory N. et al., "Shortcomings of Using Two Jet Nebulizers in Tandem with an Aerosol Face Mask for Optimal Oxygen Therapy," Chest, vol. 99, 1991, pp. 1346-1351.
Gaon, P. et al., "Assessment of effect of nasal continuous positive pressure on laryngeal opening using fibre optic laryngoscopy," Arch. Dis. Child Fetal Neonatal Ed., vol. 80, 1999, pp. F230-F232.
Geller, David E. et al., "Efficiency of Pulmonary Administration of Tobramycin Solution for Inhalation in Cystic Fibrosis Using an Improved Drug Delivery System," Chest, vol. 123, 2003, pp. 28-36.
Glasser, Stephan W. et al., "cDNA and deduced amino acid sequence of human pulmonary surfactant-associated proteolipid SPL(Phe)," Proc. Natl. Acad. Sci. USA, vol. 84, Biochemistry, Jun. 1987, pp. 4007-4011.
Hopp, Thomas P. et al., "Prediction of protein antigenic determinants from amino acid sequences," Proc. Natl. Acad. Sci. USA, vol. 78, No. 6, Immunology, Jun. 1981, pp. 3824-3828.
International Preliminary Report on Patentability for International Application No. PCT/US2009/037409, dated Sep. 21, 2010, 6 pages.
International Search Report and Written Opinion of the International Searching Authority for International Application No. PCT/US2009/037409, dated May 12, 2009, 6 pages.
International Search Report for PCT/IB2004/000333 filed Feb. 10, 2004.
International Search Report in International Application No. PCT/IB2006/001027, dated Sep. 21, 2006, 6 pages.
Kattwinkel, John MD et al., "Technique for Intrapartum Administration of Surfactant without Requirement for an Endotracheal Tube," Original Article, Journal of Perinatology, vol. 24, 2004, pp. 360-365.
Ma, Jingwen et al., "Effects of a Cationic and Hydrophobic Peptide, KL4, on Model Lung Surfactant Lipid Monolayers," Biophysical Journal, vol. 74, Apr. 1998, pp. 1899-1907.
Nguyen, Tung et al., "Generation and Characterization of Soft-Mist Aerosols from Aqueous Formulations Using the Capillary Aerosol Generator," Journal of Aerosol Medicine, vol. 16(2), Poster Presentations, Therapeutic Aerosols, Jul. 2004, p. 189.
Reply to Oct. 6, 2008 Office Action filed Jan. 5, 2009 for U.S. Appl. No. 10/774,751, 14 pages.
Richardson, C. et al., "Effect of continuous positive airway pressure on pulmonary function and blood gases of infants with respiratory distress syndrome," Pedial. Res., 1978, vol. 12, pp. 771-774.
Rosenfeld, Warren N. et al., "Water intoxication: A complication of nebulization with nasal CPAP," The Journal of Pediatrics, vol. 89, No. 1, Jul. 1976, pp. 113-114.
Salmon, B. et al., "How much aerosol reaches the lungs of wheezy infants and toddlers?," Archives of Disease in Childhood, vol. 65, 1990, pp. 401-403.
Smedsaas-Löfvenberg A. et al., "Nebulization of drugs in a nasal CPAP system," Acta. Pædiatr., vol. 88, 1999, pp. 89-92.
Thomson, Merran A. et al., "Treatment of Immature Baboons for 28 Days with Early Nasal Continuous Positive Airway Pressure," Am. J. Respir. Crit. Care Med., vol. 169, 2004, pp. 1054-1062.
Trevisanuto, Daniele et al., "Laryngeal Mask Airway Used as a Delivery Conduit for the Administration of Surfactant to Preterm Infants with Respiratory Distress Syndrome," Biology of the Neonate, vol. 87, 2005, pp. 217-220.
Verder, Henrik et al., "Nasal Continuous Positive Airway Pressure and Early Surfactant Therapy for Respiratory Distress Syndrome in Newborns of Less Than 30 Weeks' Gestation," Pediatrics, Official Journal of the American Academy of Pediatrics, vol. 103(2), 1999, pp. 1-6.
Verder, Henrik et al., "Surfactant Therapy and Nasal Continuous Positive Airway Pressure for Newborns with Respiratory Distress Syndrome," Danish-Swedish Multicenter Study Group, N. Eng. J. Med., vol. 331, No. 6, 1994, pp. 1051-1055.
Written Opinion in International Application No. PCT/IB2006/001027, dated Sep. 21, 2006, 8 pages.
Written Opinion of the International Searching Authority for PCT/IB2004/000333 filed Feb. 10, 2004.

* cited by examiner

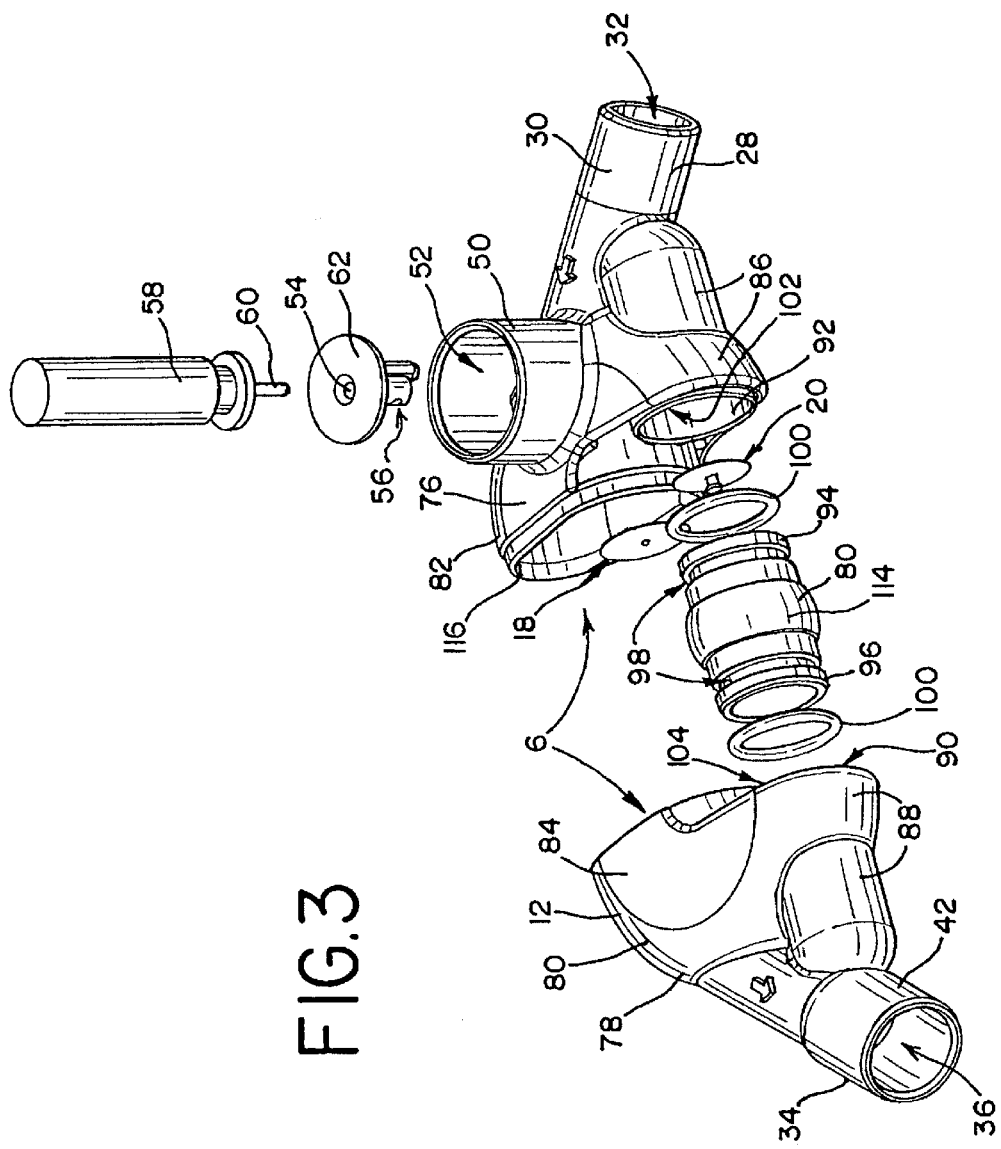

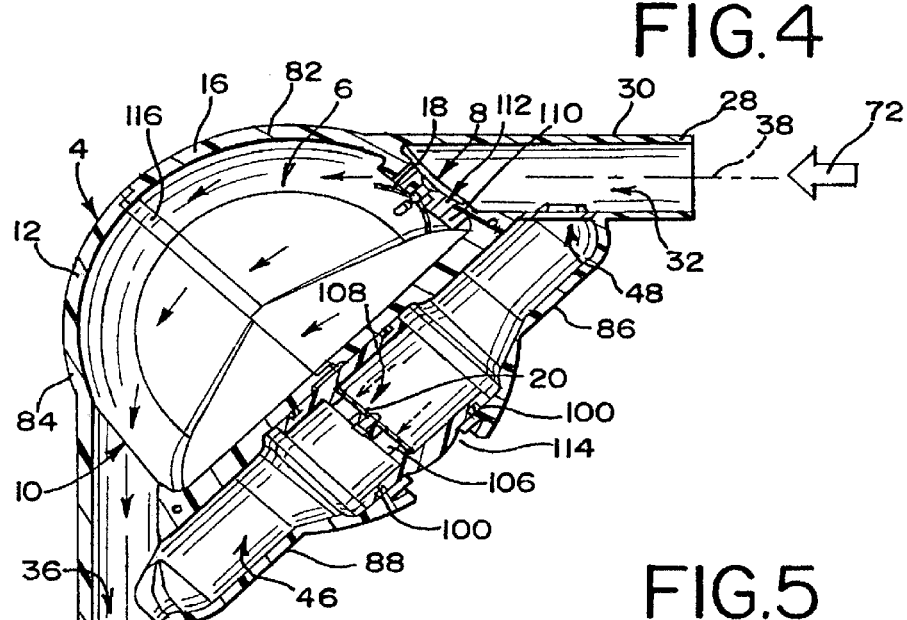
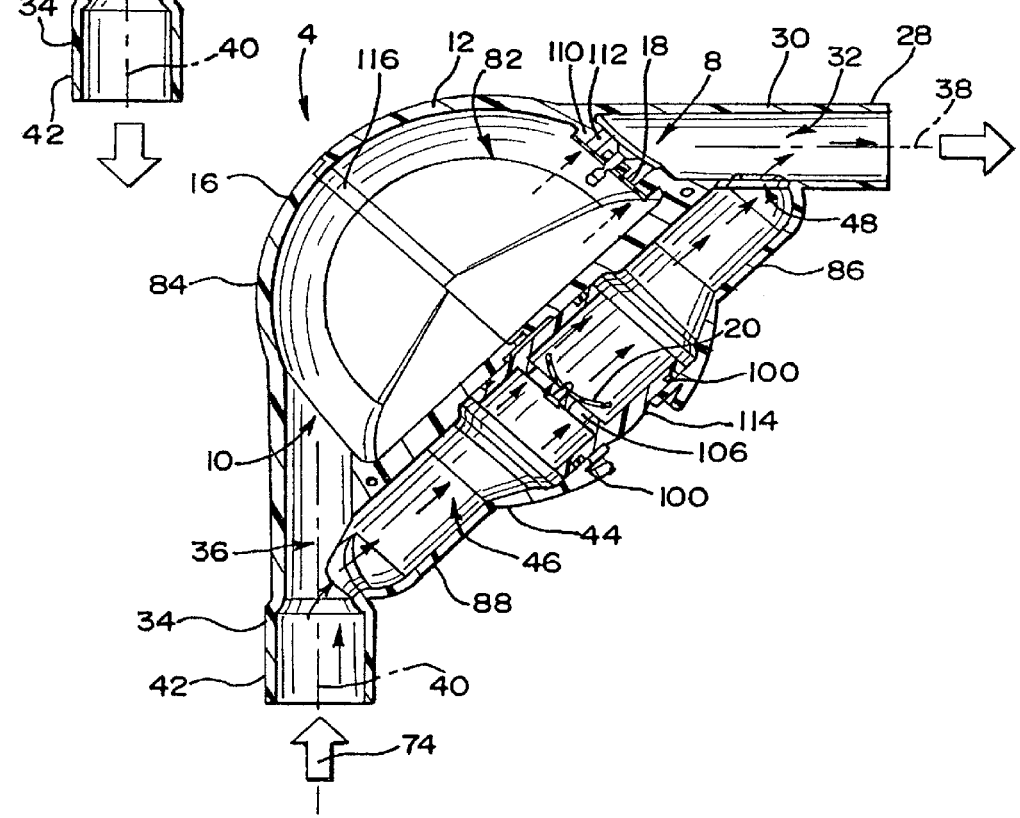

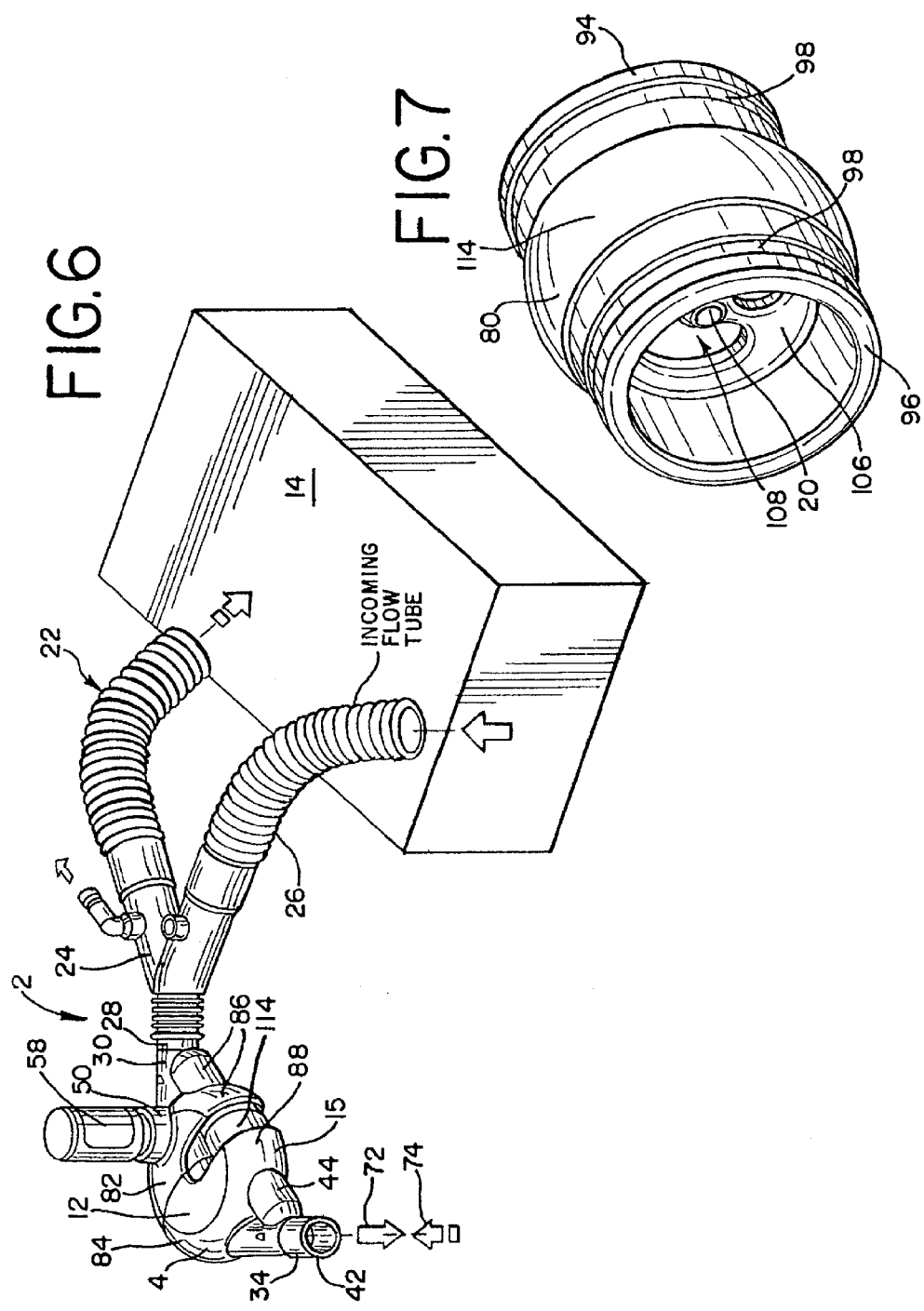

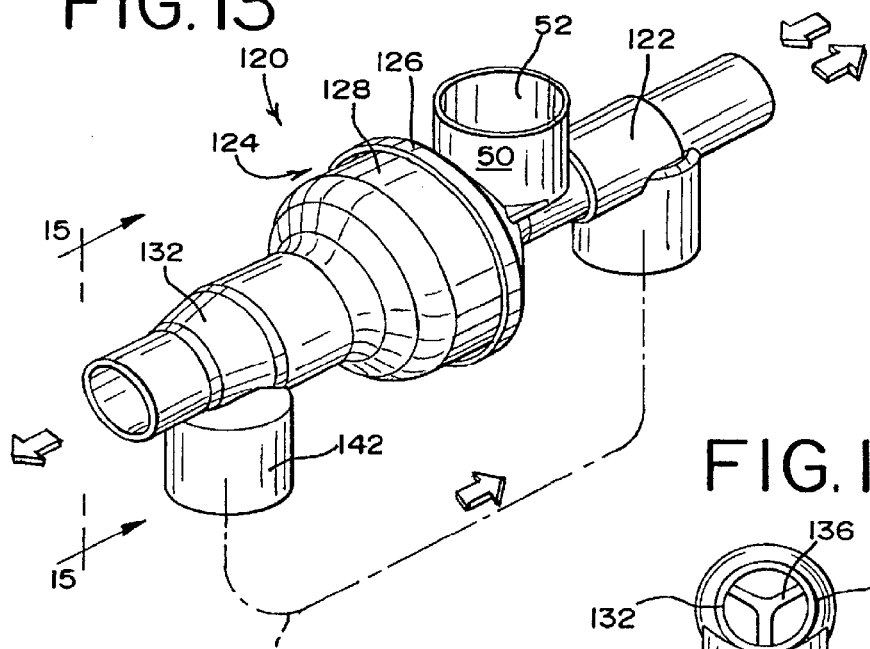
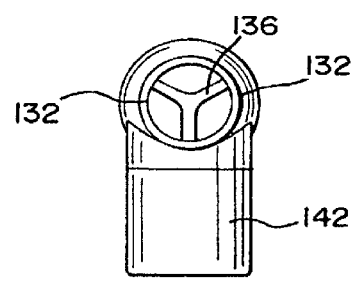
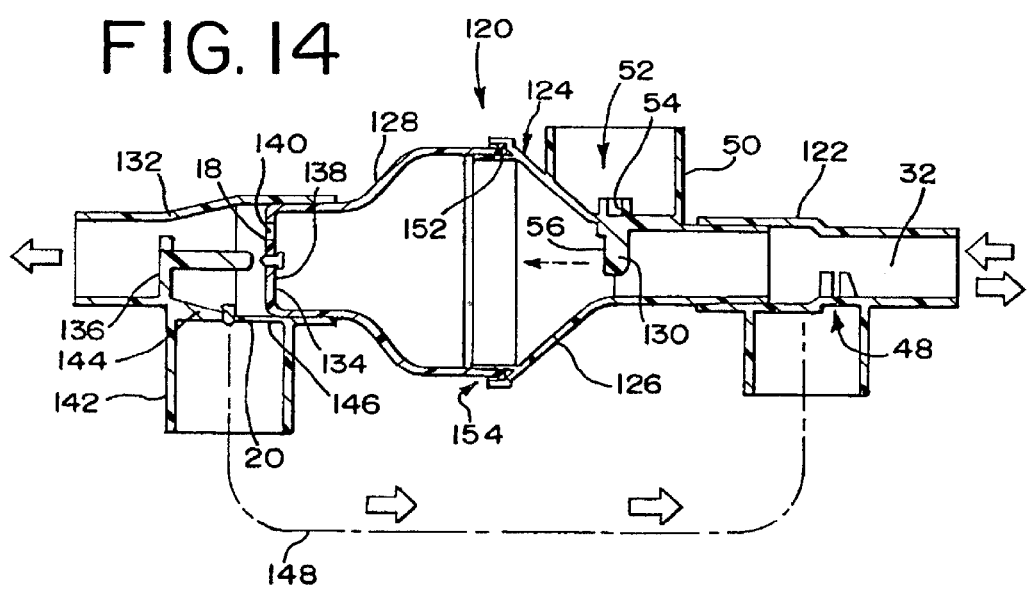

VENTILATOR CIRCUIT AND METHOD FOR THE USE THEREOF

This application is a continuation of U.S. application Ser. No. 13/231,298, filed Sep. 13, 2011, which is a continuation of U.S. application Ser. No. 11/410,270, filed Apr. 24, 2006, now U.S. Pat. No. 8,028,697, which claims the benefit of U.S. Provisional Application No. 60/675,944, filed Apr. 28, 2005, the entire disclosures of which are hereby incorporated herein by reference.

FIELD OF THE INVENTION

The present invention relates generally to a ventilator circuit, and in particular, to a ventilator circuit having inhalation and exhalation valves.

BACKGROUND

Patients have certain conditions that can be treated with medicaments dispensed in an aerosol and administered to the patient by inhalation. In one format, the aerosol and medicaments are contained in a container, and dispensed in metered, or measured, dosages with an inhalation device. For example, as shown in U.S. Pat. No. 6,435,177, entitled AEROSOL MEDICATION DELIVERY APPARATUS AND SYSTEM, and assigned to Trudell Medical International, the same Assignee as the present application, a holding chamber can be used to facilitate the administration of the medication to a patient. Typically, when used in a ventilation circuit, the holding chamber is introduced into the ventilation circuit just prior to the administration of the medication and is then removed.

SUMMARY

In one aspect, a ventilator chamber, for use in a ventilator circuit that administers medication to a patient, includes a housing, a one-way inhalation valve and a one-way exhalation valve. The housing includes a chamber defining an interior space having an input opening and an output opening, an input port defining an input passageway communicating with the input opening and adapted to receive a flow of gases from a ventilator intake line, a pressurized metered dose inhaler receptacle in fluid flow communication with the interior space, an output port defining an output passageway and communicating with the output opening; and an exhaust conduit communicating between the output passageway and the input passageway of the output port and said input port respectively. The one-way inhalation valve is positioned to permit one-way flow from the input passageway of the input port to the interior space of the chamber housing. The one-way exhaust valve is located in the exhaust conduit and is adapted to prevent a backflow of gas from the exhaust conduit into the output passageway.

In one embodiment, the input port and the output port are oriented in a substantially non-parallel relationship. In one embodiment, the input port and the output port are oriented in a substantially perpendicular relationship. This relationship allows for better positioning of the apparatus relative to the ventilator and patient.

In another aspect, a ventilator circuit for administering medication to a patient includes the chamber housing. The exhaust conduit opens directly into the input passageway at an exhaust opening formed in the input port. The one-way inhalation valve is positioned downstream from the exhaust opening. The one-way exhaust valve is located in the exhaust conduit and is adapted to prevent a backflow of gas from said exhaust conduit into said output passageway.

In another aspect, ventilator circuit includes a chamber housing defining an interior space, a one-way inhalation valve operative to permit a flow of gases into an interior space of said chamber housing, an inhalation conduit communicating with an output end of a chamber and an exhaust conduit communicating with the inhalation conduit. The exhaust conduit includes a viewing window, which permits the user or caregiver to monitor the patient's breathing cycle. A one-way exhaust valve is located in the exhaust conduit and is adapted to prevent a backflow of gas from the exhaust conduit into the inhalation conduit. At least a portion of the one-way exhaust valve is visible through the viewing window of the exhaust conduit.

In another aspect, a medication delivery device includes a holding chamber having an input end and an output end and a metered dose inhaler receptacle in communication with the input end of the holding chamber. The receptacle includes at least first and second wells shaped to receive respectively a valve stem of first and second metered dose inhalers. The first and second or orifices may have two different shapes respectively if two different medications are being used.

In yet another aspect, a method of assembling a ventilator chamber for use in a ventilator circuit includes providing a first chamber component defining at least a portion of a chamber, at least a portion of an input port and at least a portion of an exhaust conduit, providing a second chamber component defining at least a portion of the chamber, at least a portion of an output port and at least a portion of the exhaust conduit and providing a connector component defining at least a portion of the exhaust conduit. The method further includes disposing the connector component between the first and second chamber components and connecting the first and second chamber components.

In yet another aspect, a method of administering a medication to a patient includes transmitting oxygen from a gas source through an inlet line, a holding chamber and an inhalation conduit to the patient during an inhalation sequence of a breathing cycle. The method further includes introducing medication into the holding chamber, preventing a substantial transmission of an exhaust gas into the holding chamber during an exhalation sequence of the breathing cycle, and transmitting a substantial portion of the exhaust gas into an exhaust conduit during the exhalation sequence. The method further includes preventing a substantial transmission of the exhaust gas from the exhaust conduit into the inhalation conduit during subsequent inhalation sequences of subsequent breathing cycles, and transmitting the exhaust gas from the exhaust conduit directly into the inlet line.

The various embodiments and aspects provide significant advantages over other ventilator circuits. In particular, the inhalation valve creates a back pressure, which prevents a substantial portion of an exhaust gas from entering the chamber. In addition, the exhaust valve also operates to prevent the exhaust gases from reentering the inhalation conduit from the exhalation conduit. In this way, the chamber can remain in the ventilator circuit even when not being used to administer a medication.

In addition, in one embodiment, the housing, with its integrated input port, output port and exhaust conduit, can be easily manufactured and installed in the ventilator circuit without the need for an additional exhaust tube or connector. Likewise, the three-piece housing, with its three components, can be easily assembled. In addition, the orientation of the input and output ports are perpendicular to allow for the positioning of the ventilator circuit beside the patient and to connect the ventilator circuit to the endotracheal tube without the need for an elbow connector.

The metered dose inhaler receptacle also provides advantages with its two wells. For example, the same chamber can be used with different medicament containers and formulations without having to remove the chamber from the circuit.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 3 is an exploded view of the ventilator chamber shown in FIG. 1.

FIG. 4 is a top, cross-sectional view of the ventilator chamber shown in FIG. 1 during an inhalation sequence of a breathing cycle.

FIG. 5 is a top, cross-sectional view of the ventilator chamber shown in FIG. 1 during an exhalation sequence of a breathing cycle.

FIG. 6 is a perspective view of a portion of a ventilator circuit.

FIG. 7 is a perspective view of a connector component.

FIG. 13 is a perspective view of another alternative embodiment of a ventilator chamber.

FIG. 14 is a cross-sectional view of the ventilator chamber shown in FIG. 13.

FIG. 15 is an end view of the output component of the ventilator chamber shown in FIG. 13.

DETAILED DESCRIPTION OF THE PRESENTLY PREFERRED EMBODIMENTS

Figure 1:
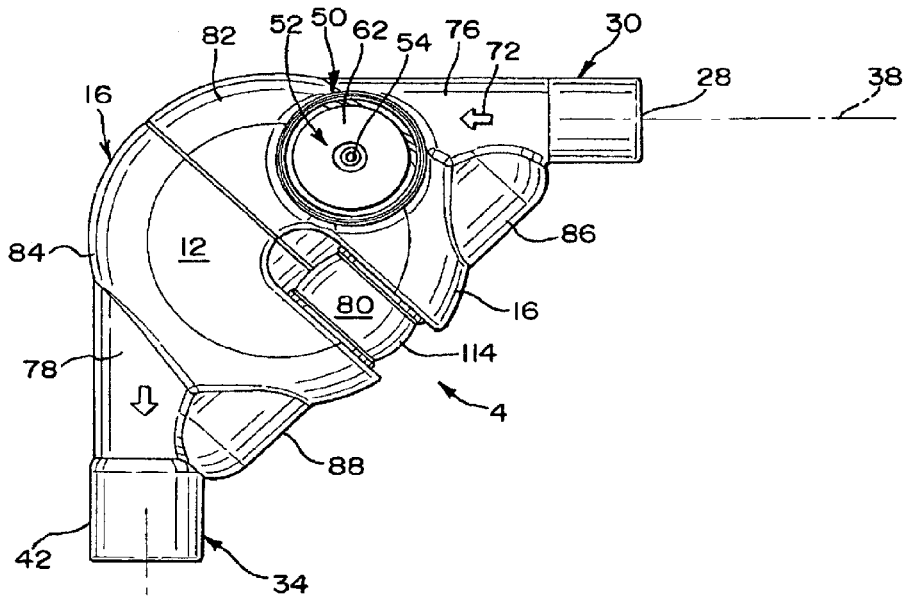
FIG. 1 is a top view of one embodiment of a ventilator chamber.
Figure 2:
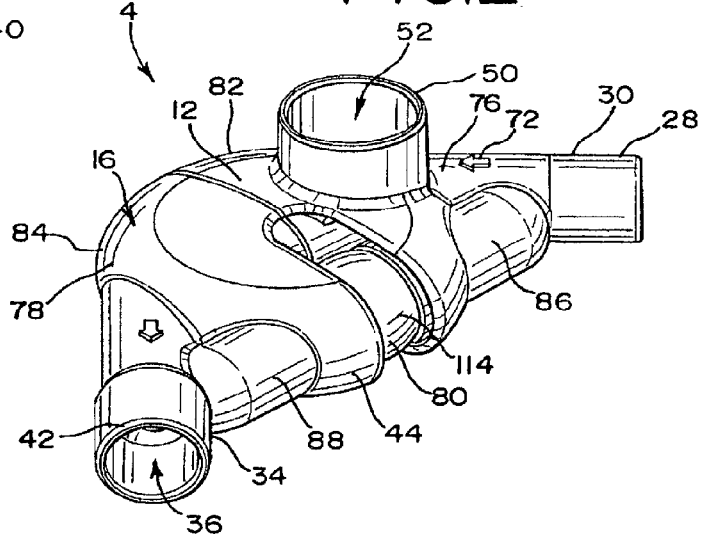
FIG. 2 is a perspective view of the ventilator chamber shown in FIG. 1.

Referring to FIGS. 1-6, a ventilator circuit 2 is shown as having a ventilator chamber 4 positioned in the inspiratory flow path from the ventilator 14 to the patient. The ventilator chamber 4 includes a housing 16 having a holding chamber 12 defining an interior space 6, an input opening 8 and an output opening 10. In one embodiment configured for an adult, the holding chamber 12, and in particular the interior space 6, preferably has a volume of between about 50 ml and 250 ml, more preferably between about 60 ml and 100 ml, and most preferably about 85 ml, although other volumes not specifically enumerated herein are suitable. In an alternative embodiment configured for an infant, child or younger patient, the volume of the interior space is between about 20 and 60 ml, and preferably about 35 ml.

Preferably, the holding chamber 12 is made of a clear plastic, although it can be non-transparent in certain embodiments. Various aspects of the holding chamber are further disclosed and described in U.S. Pat. No. 6,435,177, which is hereby incorporated herein by reference in its entirety. In one embodiment, the holding chamber is made from an anti-static material, as disclosed for example and without limitation in U.S. patent application Ser. No. 10/821,260, filed Apr. 8, 2004, which is hereby incorporated herein by reference in its entirety. In one embodiment, the holding chamber is antistatic, meaning it has a surface resistivity of less than about 10E12 ohm/sq., and preferably between about 10E10 and about 10E12 ohm/sq. Preferably the anti-static holding chamber is made of plastic. The holding chamber 12 has a one-way inhalation valve 18 positioned upstream of the interior space 6, and a one-way exhaust valve 20 positioned downstream of the interior space 6. As used herein, "upstream" and "downstream" refer to the direction of the flow of gases during the inhalation sequence of a breathing cycle. As used herein, the terms "exhaust" and "exhalation" are interchangeable.

The ventilator circuit further includes a ventilator intake line 26, which forms part of an inhalation conduit that runs between the ventilator and the holding chamber. The intake line 26 carries oxygen from the ventilator 14 to a Y-connector 24, which is also connected to an exhaust line 22. The Y-connector 24 also is connected to an input end 28 of an input port 30 of the ventilator housing. The input port defines an input passageway 32 in communication with the input opening 8 of the housing chamber. The terms "communicate," "communicates," "communication," and variations thereof, refer to the conveyance of a fluid, e.g., liquid or gas, between two components or locations, whether directly or indirectly, for example by way of another component.

The housing further includes an output port 34 having an output passageway 36 in communication with the output opening 10 of the holding chamber 12. As shown in FIGS. 1-6, the input port 30 and output port 34, and the respective input and output passageways 32, 36, each defined by axes 38, 40 respectively, are configured in a non-parallel relationship, and in one embodiment in a substantially perpendicular relationship.

In various embodiments, the output port 34 of the ventilator chamber can be configured with a narrow orifice in the output passageway, as disclosed for example in U.S. Provisional patent application Ser. No. 10/979,743, filed Nov. 2, 2004 and entitled AEROSOL MEDICATION DELIVERY APPARATUS WITH NARROW ORIFICE, which is hereby incorporated by reference herein. In one embodiment, the narrow orifice is formed integrally in the output port. In another embodiment, the narrow orifice is formed in an adapter secured to the ventilation chamber 4. The narrow orifice, when formed for example in an adapter, is positioned between the output port 34 and a user interface element (not shown) connected thereto. In one exemplary embodiment, the narrow orifice has a cross-sectional area of less than about 60 mm$^2$.

The output port 34 has an end portion 42 configured to mate with a patient or user interface element, configured for example as a mask, mouthpiece or endotracheal tube. The patient interface element completes the inhalation conduit. The patient interface element preferably includes an end portion configured to be disposed in or around the end portion 42 of the output port. Alternatively, the patient interface element can be integrally formed with the output port.

The housing further includes an exhalation conduit 44 that extends between and is connected to the input and output ports 30, 34. The exhalation conduit defines a passageway 46 that communicates with the input and output passageways 32, 36. In one embodiment, the exhaust conduit passageway 46 opens directly into the input passageway through an exhaust opening.

A pressurized metered dose inhaler (MDI) receptacle 50 is formed on a top of the housing 16. The receptacle 50 defines a socket or recess 52 shaped to receive the end portion of a medicament container 58 and a well 54 formed in the bottom of the recess. The well 54 is shaped to receive and frictionally engage a valve stem 60 extending from the end of the container. The well 54 communicates with an orifice 56, which opens into the interior space of the chamber. In one embodiment, the well 54 and orifice 56 are defined by a discharge nozzle 62, which is removably secured in the bottom of the receptacle. An arm or locator member extends from the nozzle to ensure the proper orientation of the nozzle and also to prevent the inhalation valve from dislodging and entering into the inhalation tube leading to the patient. Since the nozzle is removeable in one embodiment, different nozzles can be exchanged and used with the same ventilation chamber 4, even without having to remove the ventilation chamber 4 from the ventilator circuit 2. It should be understood that the receptacle can be configured to connect to and support medication containers or systems other than the disclosed MDI.

Figure 8:
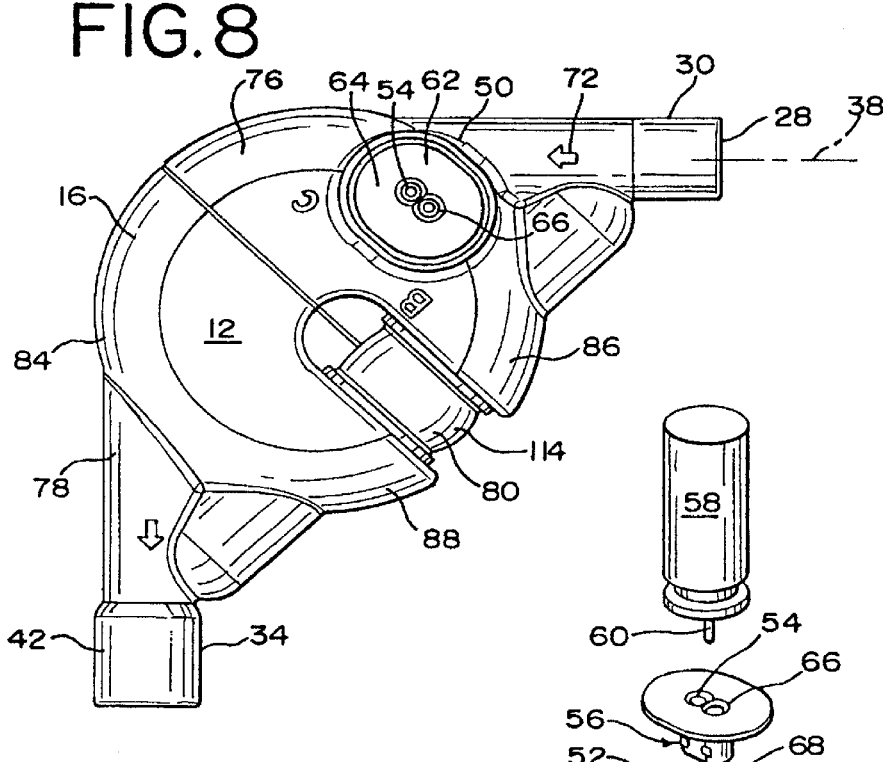
FIG. 8 is a top view of an alternative embodiment of a ventilator chamber.
Figure 9:
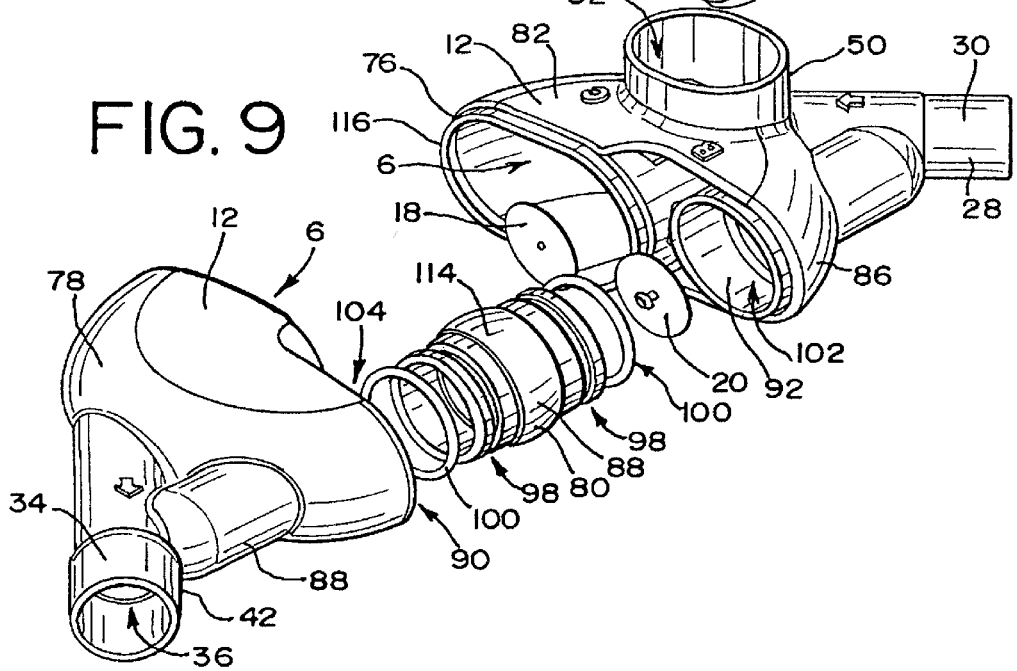
FIG. 9 is an exploded perspective view of the ventilator chamber shown in FIG. 8.

Referring to the embodiment of FIGS. 8 and 9, the discharge nozzle 64 has a plurality (meaning more than one) of wells 54, 66 and respective orifices 56, 68. The recess 5 and nozzle have an obround shape, rounded at opposite ends to accommodate a container in each well. In one embodiment, the wells are spaced such that the containers can be mounted simultaneously in tandem, while in another embodiment they must be mounted sequentially. In the illustrated embodiment, the nozzle has a first and second well 54, 66. The wells 54, 66 communicate with respective orifices 56, 68, which have different shapes. The different orifices accommodate different types of medication. In particular, the size of the orifice will influence the size of the aerosol particle. For certain medications targeted for the deep part of the lungs, a particle size of about 4.7 microns is desirable. Other medications target the upper part of the lungs, and may therefore have a particle size desirably greater than 4.7 microns. In one embodiment, a first orifice is about 11 microns, suitable for example and without limitation for corticosteroid medication, and the second orifice is about 14 microns, suitable for example and without limitation for bronchodilator medication.

It should be understood that the wells can also have a different shape top accommodate different shapes of valve stems. It should be understood that the wells can have the same shape, with the orifices being configured differently for different formulations, that the orifices can have the same shape with the wells having a different shape, or with both the orifices and wells having a different shape. It should be understood that the phrase "different shape" means a different cross-sectional configuration, for example and without limitation circular or polygonal, or a different cross-sectional area, for example and without limitation circular orifices having different diameters.

Figure 10:
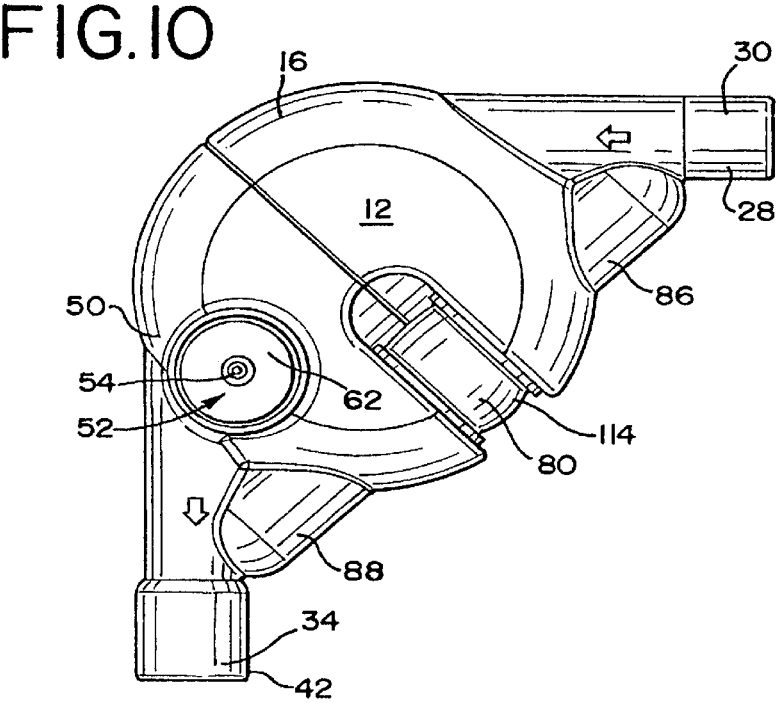
FIG. 10 is a top view of another alternative embodiment of a ventilator chamber.
Figure 11:
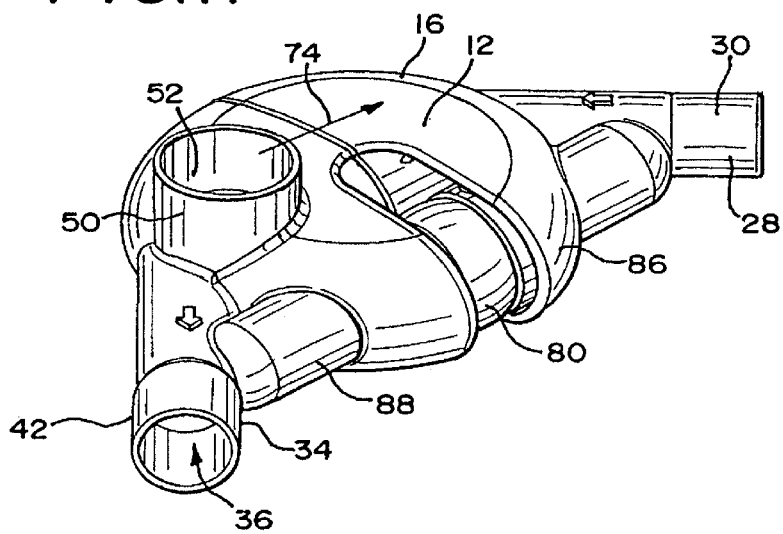
FIG. 11 is a perspective view of the ventilator chamber shown in FIG. 10.
Figure 12:
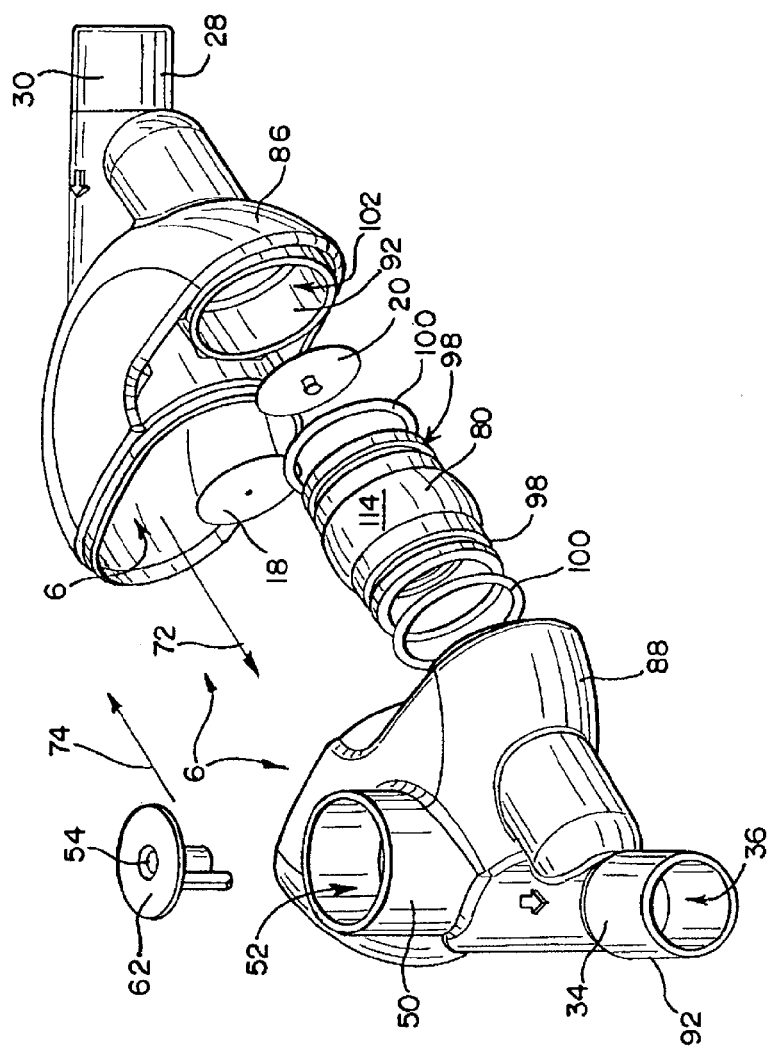
FIG. 12 is an exploded view of the ventilator chamber shown in FIG. 10.

In the embodiments of FIGS. 1-6, 8 and 9, the orifice(s) 56, 68 is positioned adjacent or proximate the input opening 8 and opens in a downstream direction 72 into the interior space 6 of the holding chamber. Alternatively, as shown in FIGS. 10-12, the MDI receptacle is positioned adjacent or proximate the output opening 10, with the orifice opening or directed in the upstream direction 74 into the interior space 6 of the chamber.

As shown in FIGS. 1-11, the ventilator chamber preferably includes three components 76, 78, 80. A first component 76 forms and defines the input port 30, a portion 82 of the holding chamber (and interior space thereof) and a portion 86 of the exhalation conduit. A second component 78 forms and defines the output port 34, a portion 84 of the holding chamber (and interior space thereof) and a portion 88 of the exhalation conduit. As shown in the respective embodiments of FIGS. 1-7 and 9-11, the MDI receptacle 50 can be configured or formed on either the first or second component 76, 78. In another embodiment (not shown), both the first and second components have a MDI receptacle formed thereon.

A third component 80, or connector component, defines in part the exhalation conduit 44. The connector component 80 extends between exhaust openings 90, 92 formed in the first and second components respectively. In one embodiment, the connector component 80 is preferably clear or see-through, and defines a viewing window in the exhalation conduit. The connector component is generally cylindrical in nature and has opposite ends 94, 96. Each end includes an annular or circumferential groove 98 formed around the periphery of the connector tube. An O-ring, or other seal member 100, is disposed in each groove 98 and mates with the interior surface of exhaust sockets 102, 104 formed in the first and second components. In this way, the seal members 100 prevent any gases from escaping from the exhaust conduit 44 to the ambient environment.

Referring to FIGS. 4 and 7, the connector component 80 includes an internal wall 106 forming a valve seat. One or more openings 108 are formed in the wall to permit passage of gases through the wall. A one-way exhalation valve member 20, shown as a center post valve is secured to a downstream side of the wall 106, with the valve covering the openings 108 when in a normal, closed position. The valve member 20 is preferably colored, for example a bright color, such that it is easily visible through the viewing window 114 of the connector component 80. The spherical shape of the viewing window 114 magnifies the appearance of the valve member 20.

A wall or valve seat 110 is also formed in the input opening of the housing chamber between the housing chamber and the input port. Again, one or more openings 112 are formed in the wall 110 to permit the flow of gases from the input passageway into the interior space of the chamber. A one-way inhalation valve member, for example a center post valve member 18, is secured to the downstream side of the wall 110 and covers the openings 112 when in a normal, at closed position. In other embodiments, the inhalation and exhalation valves can be configured as a duckbill valve, or other known one-way valves.

In operation, and referring to FIGS. 4 and 5, during the inhalation sequence of a breathing cycle, the ventilator 14 introduces or transmits oxygen from a gas source through the intake line 26, input passageway and one-way inhalation valve, defined in one embodiment by the valve member 18 and valve seat 110. A user, such as a doctor or nurse, actuates the medicament container 58 by depressing the container towards the receptacle 50, which releases a metered dose of medicament into the interior space 6 of the holding chamber 12. The medicament travels with the oxygen through the output opening 10 of the holding chamber and through the inhalation conduit, formed at least in part by the output passageway 36 in the outlet port 34 and the patient interface element.

During the exhalation sequence of the breathing cycle, exhaust gases are expelled from the lungs through the patient interface element back into the output port 34. Since the one-way inhalation valve, including in one embodiment the valve member 18 and valve seat 110 positioned upstream of the output port 34, prevents the flow of gases back into the input port 30, the one-way inhalation valve creates a back pressure in the holding chamber 12, thereby preventing a substantial amount of exhaust gases from entering the holding chamber 12. Instead, a substantial amount of the exhaust gases are transmitted through the exhaust conduit 44 past the one-way exhalation valve, formed in one embodiment by the valve member 20 and valve seat 106. As the gases pass the one-way exhalation valve, the user or care-giver monitors the viewing window 114 to determine whether the valve member 20 is moving, thereby confirming that the system is working properly. The exhaust gases pass through the exhaust conduit 44 through the exhaust opening 48 into the input passageway 32 formed by the input port. The gases then travel through the Y-connector 24 and into the exhaust line 22 to the ventilator. Upon the next inhalation sequence of the breathing cycle, the one-way exhalation valve 20, 110 prevents the exhaust gases in the exhaust conduit 44 positioned downstream from the one-way exhaust valve 20, 110 from reentering the inhalation conduit, including the output passageway 36. By introducing the exhaust gases into the input passageway 32, the humidity of the exhaust gases is deposited at the connection point 28 to a humidifier filter exchanger thereby humidifying the dry gas flow coming from the intake line 26 and ventilator 14. In this way, the relatively short exhalation conduit 44, which is integrated into the ventilator chamber 4, shortens the distance the exhaust gases have to travel and thereby increase the level of humidity at the input side of the housing.

A gas analyzer, shown for example in U.S. Pat. No. 5,693,944, which is hereby incorporated herein by reference, can be connected to the exhaust line or Y-connector to monitor the amount of CO2 gas or other gases are flowing through the conduit. A pressure line port 118 can also be connected to the Y-connector to monitor the gas pressure in the circuit to avoid any increase in pressure due to an obstruction in the system, for example and without limitation.

Preferably, the ventilation chamber housing components 76, 78, 80 are made of a hard plastic, including for example and without limitation ABS, polypropylene, polyethylene, metal or PVC. Preferably, the valve members are made of a flexible material, including for example and without limitation polypropylene, polyethylene, silicone, thermoplastic elastomers, EPDM, and rubber. Various aspects of the ventilator circuit and components are disclosed and shown in U.S. patent application Ser. No. 10/774,751, filed Feb. 9, 2004, the entire disclosure of which is hereby incorporated herein by reference.

One of the first and/or second components 76, 78 has a peripheral flange 116 or step that mates with the other component as the third component 80 is sandwiched between the first and second components 76, 78. The first and second components can be bonded, or otherwise connected for example by welding, snap-fit, or other known devices. The receptacle is preferably integrally molded with one or the other (or both) of the first and second components 76, 78.

Referring to FIGS. 13-15, a four-piece ventilator chamber 120 is shown. An input port component 122 is connected to an input end of a holding chamber component 124. In one embodiment, the holding chamber is formed from two pieces 126, 128, with the MDI receptacle positioned on one of the holding chamber components. The components 126, 128 are snap-fit together with a circumferential ring 152 that fits in a corresponding groove 154. A discharge nozzle 130 extends into an input passageway 32 and includes an orifice 56 facing downstream. The input component 122 has an exhaust opening communicating with the input passageway.

An output port 132 is connected to the output end 134 of the holding chamber. The output end includes a wall 138 having one or more openings 140 formed therethrough. The wall defines a valve seat for a one-way inhalation valve. The valve member 18 is connected to the wall on the downstream side thereof. The output port 132 has a baffle formed therein to prevent the valve member 18 from becoming dislodged and making its way to the patient, and is shown in one embodiment as a three arms 136. The baffle includes an arm portion extending upstream to prevent the valve dislodgement.

An exhaust conduit 142 communicates with the output passageway and has a wall 144 formed at a junction thereof. The wall has one or more openings 146 formed therein to permit the passage of gases through the wall. The wall defines in part a valve seat. A one-way exhalation valve member 20 is connected to the valve seat downstream therefrom. A tubular exhaust line 148, separate from or integral with, one or both of the input and output ports 122, 132 connects the ports and completes the exhaust conduit.

In operation, the ventilator chamber 120 operates in the same way as the embodiments shown in FIGS. 1-12. In particular, the one-way inhalation valve 138, 18 permits only one-way flow of gas and medicament to the patient, while the one-way exhalation valve 144, 20 prevents exhaust gases from reentering the inhalation conduit downstream of the holding chamber 124. In the embodiment of FIGS. 13-15, however, the one-way inhalation valve 138, 18 is positioned downstream of the holding chamber 124, rather than upstream thereof. In addition, the exhaust conduit communicates directly with the input passageway and thereby provides passive humidification of the input gases entering the holding chamber.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A ventilator chamber for use in a ventilator circuit for administering medication to a patient, the ventilator chamber comprising:
   a housing comprising:
      a chamber defining an interior space having an input opening and an output opening;
      an input port defining an input passageway communicating with said input opening and adapted to receive a flow of gases from a ventilator intake line, said input port further comprising an inlet spaced apart from said input opening and formed at an end of said input port;
      a metered dose inhaler receptacle in fluid flow communication with said interior space;

an output port defining an output passageway communicating with said output opening, said output port further comprising an outlet spaced apart from said output opening and formed at an end of said output port; and an exhaust conduit communicating between and directly with said output passageway of said output port and said input passageway of input port;

wherein an inhalation pathway having a first length is defined from said inlet to said outlet through said input passageway, said interior space and said output passageway; and wherein an exhalation pathway having a second length is defined from said outlet to said inlet through said output passageway, said exhaust conduit and said input passageway, wherein said second length is less than said first length.

2. The ventilator chamber of claim 1 further comprising a one-way inhalation valve positioned to permit one-way flow from said input passageway of said input port to said interior space of said chamber housing.

3. The ventilator chamber of claim 2 further comprising a one-way exhaust valve located in said exhaust conduit, said one-way exhaust valve adapted to prevent a backflow of gas from said exhaust conduit into said output passageway.

4. The ventilator chamber of claim 1 wherein said exhaust conduit is linear.

5. The ventilator chamber of claim 4 wherein said interior space is defined in part by a linear wall spaced apart from a curved wall when said chamber is viewed in cross section.

6. The ventilator chamber of claim 5 wherein said linear wall separates said exhaust conduit and said interior space.

7. The ventilator chamber of claim 1 wherein at least a portion of said chamber, said input port and said exhaust conduit are integrally formed as a one-piece unit.

8. The ventilator chamber of claim 1 wherein at least a portion of said chamber, said output port and said exhaust conduit are integrally formed as a one-piece unit.

9. The ventilator chamber of claim 1 wherein at least a portion of said chamber, said input port, said output port and said exhaust conduit are integrally formed as a one-piece unit.

10. The ventilator chamber of claim 1 wherein at least a portion of said chamber, said output port and at least a portion of said exhaust conduit are integrally formed as a first component, wherein at least a portion of said chamber, said input port, and at least a portion of said exhaust conduit are integrally formed as a second component separate from said first component, and wherein at least a portion of said exhaust conduit is formed as a third component separate from said first and second components, wherein said first and second components are connected to define said interior space of said chamber and with said third component connected between said first and second components.

11. The ventilator chamber of claim 1 wherein said exhaust conduit comprises a viewing window, wherein at least a portion of a one-way exhalation valve is visible through said viewing window.

12. The ventilator chamber of claim 1 wherein said metered dose inhaler receptacle opens into and communicates directly with said interior space.

13. The ventilator chamber of claim 12 wherein said metered dose inhaler receptacle is positioned adjacent said input opening and comprises an orifice oriented in a downstream direction.

14. The ventilator chamber of claim 12 wherein said metered dose inhaler receptacle is positioned adjacent said output opening and comprises an orifice oriented in an upstream direction.

15. The ventilator chamber of claim 1 wherein at least a portion of said housing is made of an antistatic material.

16. The ventilator chamber of claim 1 further comprising a metered dose inhaler disposed in said metered dose inhaler receptacle, said metered dose inhaler comprising a medication dispensed in aerosol form.

17. The ventilator chamber of claim 1 wherein said input passageway is oriented along a first axis, said output passageway is oriented along a second axis, and at least a portion of said exhaust conduit is oriented along a third axis, wherein said third axis forms an acute angle with each of said first and second axes.

* * * * *